US009415381B2

(12) United States Patent
Burton (10) Patent No.: US 9,415,381 B2
(45) Date of Patent: Aug. 16, 2016

(54) EMM-22 MOLECULAR SIEVE, ITS SYNTHESIS AND USE (75) Inventor: Allen W. Burton, Stewartsville, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 302 days.

(21) Appl. No.: 14/236,376
(22) PCT Filed: Jul. 24, 2012
(86) PCT No.: PCT/US2012/047908
§ 371 (c)(1),
(2), (4) Date: Mar. 12, 2014
(87) PCT Pub. No.: WO2013/028303
PCT Pub. Date: Feb. 28, 2013

(65) Prior Publication Data
US 2014/0200386 A1 Jul. 17, 2014

Related U.S. Application Data
(60) Provisional application No. 61/525,534, filed on Aug. 19, 2011.

(30) Foreign Application Priority Data
Sep. 30, 2011 (EP) .................................. 11183530

(51) Int. Cl.
C01B 39/48 (2006.01)
B01J 29/70 (2006.01)
C07C 7/13 (2006.01)
(Continued)

(52) U.S. Cl.
CPC *B01J 29/70* (2013.01); *B01J 20/18* (2013.01); *B01J 20/28071* (2013.01); *B01J 20/28097* (2013.01); *B01J 20/3078* (2013.01); *B01J 20/3085* (2013.01); *B01J 35/002* (2013.01);
(Continued)

(58) Field of Classification Search
CPC ............ C01B 39/48; C07C 7/13; B01J 29/70; B01J 35/002; B01J 2229/42
See application file for complete search history.

(56) References Cited

U.S. PATENT DOCUMENTS 3,354,078 A 11/1967 Miale et al.
4,910,006 A 3/1990 Zones et al.
(Continued)

FOREIGN PATENT DOCUMENTS

EP 0 135 658 4/1985
WO 2010/065318 6/2010

OTHER PUBLICATIONS

Baerlocher et al., *Atlas of Zeolite Framework Types*, 6th Revised Edition, Elsevier, 2007.

(Continued)

*Primary Examiner* — David M Brunsman
(74) *Attorney, Agent, or Firm* — Darryl M. Tyus

(57) ABSTRACT

A molecular sieve material designated as EMM-22 has, in its calcined form, an X-ray diffraction pattern including the following peaks in Table 1:

TABLE 1

| d-spacing (Å) | Relative Intensity [100 × I/I(o)] |
|---|---|
| 11.03 ± 0.40 | VS |
| 9.91 ± 0.20 | W |
| 6.70 ± 0.04 | VW |
| 4.39 ± 0.02 | W |
| 4.06 ± 0.04 | W |
| 3.85 ± 0.02 | M |
| 3.37 ± 0.02 | W |

14 Claims, 3 Drawing Sheets (51) Int. Cl.
  *B01J 20/18* (2006.01)
  *B01J 20/28* (2006.01)
  *B01J 20/30* (2006.01)
  *B01J 35/00* (2006.01)

(52) U.S. Cl.
  CPC . *C01B 39/48* (2013.01); *C07C 7/13* (2013.01); *B01J 2229/42* (2013.01)

(56) References Cited

U.S. PATENT DOCUMENTS

| | | | |
|---|---|---|---|
| 4,941,963 | A | 7/1990 | Valyocsik |
| 4,963,337 | A | 10/1990 | Zones |
| 5,007,997 | A | 4/1991 | Zones et al. |
| 5,120,425 | A | 6/1992 | Zones et al. |
| 6,136,290 | A | 10/2000 | Benazzi et al. |
| 7,648,694 | B2 | 1/2010 | Burton, Jr. |
| 2009/0060835 | A1* | 3/2009 | Burton, Jr. ............... B01J 29/70 423/706 |
| 2013/0330271 | A1* | 12/2013 | Elomari ................. C01B 39/48 423/704 |

OTHER PUBLICATIONS

Treacy et al., *Collection of Simulated XRD Powder Patterns for Zeolites*, Fifth Revised Edition, Elsevier, 2007.

Jackowski et al., "*Diquaternary Ammonium Compounds in Zeolite Synthesis: Cyclic and Polycyclic N-Heterocycles Connected by Methylene Chains*", Journal of the American Chemical Society, vol. 131, No. 3, Jan. 7, 2009; pp. 1092-1100.

Lee et al., "*Synthesis and Characterization of ERI-Type UZM-12 Zeolites and Their Methanol-to-Olefin Performance*", Journal of the American Chemical Society, vol. 132, No. 7, Sep. 22, 2010, pp. 12971-12982.

Lobo et al., "*SSZ-26 and SSZ-33: Two Molecular Sieves with Intersecting 10- and 12-Ring Pores*", Science, vol. 262, No. 5139, Dec. 3, 1993, pp. 1543-1546.

Maple et al., "*Synthesis and characterisation of aluminophosphate-based zeotype materials prepared with α, ω-bis(N-methylpyrrolidinium) alkane cations as structure-directing agents*", Dalton Transactions 2007, The Royal Society of Chemistry, No. 37, Oct. 7, 2007, pp. 4175-4181.

Miale et al., "Catalysis by Crystalline Aluminosilicates—IV. Attainable Catalytic Cracking Rate Constants, and Superactivity", Journal of Catalysis 6, pp. 278-287 (1966).

Olson et al., "Chemical and Physical Properties of the ZSM-5 Substitutional Series", Journal of Catalysis 61, pp. 390-396 (1980).

Parikh et al., "Non-thermal calcination by ultraviolet irradiation in the synthesis of microporous materials", Microporous and Mesoporous Materials 76 (2004), pp. 17-22.

Weisz et al., "Superactive Crystalline Aluminosilicate Hydrocarbon Catalysts", Journal of Catalysis 4, pp. 527-529 (1965).

Treacy et al., *Collection of Simulated XRD Powder Patterns for Zeolites*, Fourth Revised Edition, Elsevier, 2001.

Periodic Table of the Elements, Feb. 4, 1985, Chemical and Engineering News, pp. 27.

\* cited by examiner

EMM-22 MOLECULAR SIEVE, ITS SYNTHESIS AND USE

CROSS REFERENCE TO RELATED APPLICATIONS

This application is a 371 National Stage Application of International Application No. PCT/US2012/047908 filed Jul. 24, 2012, which claims the benefit of and priority to U.S. Patent Application No. 61/525,534 filed Aug. 19, 2011, the disclosures of which are incorporated herein by reference in their entireties.

FIELD

This invention relates to a novel molecular sieve material, designated as EMM-22, its synthesis, its use as an adsorbent, and a catalyst for hydrocarbon conversions.

BACKGROUND

Molecular sieve materials, both natural and synthetic, have been demonstrated in the past to be useful as adsorbents and to have catalytic properties for various types of hydrocarbon conversion reactions. Certain molecular sieves, zeolites, AlPOs, mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional frameworks of $SiO_4$ and Periodic Table Group 13 element oxide (e.g., $AlO_4$). The tetrahedra are cross-linked by the sharing of oxygen atoms whereby the ratio of the total Group 13 element (e.g., aluminum) and silicon atoms to oxygen atoms is 1:2. The electrovalence of the tetrahedra containing the Group 13 element (e.g., aluminum) is balanced by the inclusion in the crystal of a cation, for example a proton, an alkali metal or an alkaline earth metal cation. This can be expressed wherein the ratio of the Group 13 element (e.g., aluminum) to the number of various cations, such as $H^+$, $Ca^{2+/2}$, $Sr^{2+/2}$, $Na^+$, $K^+$, or $Li^+$, is equal to unity.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference. A large pore zeolite generally has a pore size of at least about 7 Å and includes LTL, MAZ, FAU, OFF, *BEA, and MOR framework type zeolites (IUPAC Commission of Zeolite Nomenclature). Examples of large pore zeolites include mazzite, offretite, zeolite L, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

SSZ-26 and SSZ-33 are known large pore zeolites which contain a three-dimensional pore system composed of intersecting 10- and 12-ring pores. (See, Lobo et al., "SSZ-26 and SSZ-33: Two Molecular Sieves with Intersecting 10- and 12-Ring Pores" Science, Vol. 262. no. 5139, pp. 1543-1546, Dec. 3, 1993). These two zeolites can be characterized as members of a family of materials in which the two end members are formed by the stacking of layers in an ABAB sequence or an ABCABC sequence. The framework formed by the ABAB stacking sequence ("polymorph A") is of orthorhombic symmetry and the framework formed by the ABCABC stacking sequence ("polymorph B") is of monoclinic symmetry. In between these end-member polymorphs there is a whole family of materials that can be characterized by a fault probability "p" of 0%<p<100% (referred to herein as "SSZ-26/33 family"). If the fault probability is p=0%, the end member polymorph B is obtained, and if p=100%, the end member polymorph A is obtained. The aluminosilicate SSZ-26 and the borosilicate SSZ-33 are members of this disordered family of materials and CIT-1 corresponds to a pure or nearly pure polymorph B. (See, CON Framework Datasheet, Baerlocher et al., Atlas of Zeolite Framework Types, 6$^{th}$ Ed. (2007)) (See also, CON powder pattern and SSZ-26/33 family, polymorph A-polymorph B powder pattern simulations of disordered intergrowths, Treacy et al., Collection of Simulated XRD Powder Patterns for Zeolites, 4th Ed., Amsterdam:Elsevier (2001)).

Figures 1A, 1E:
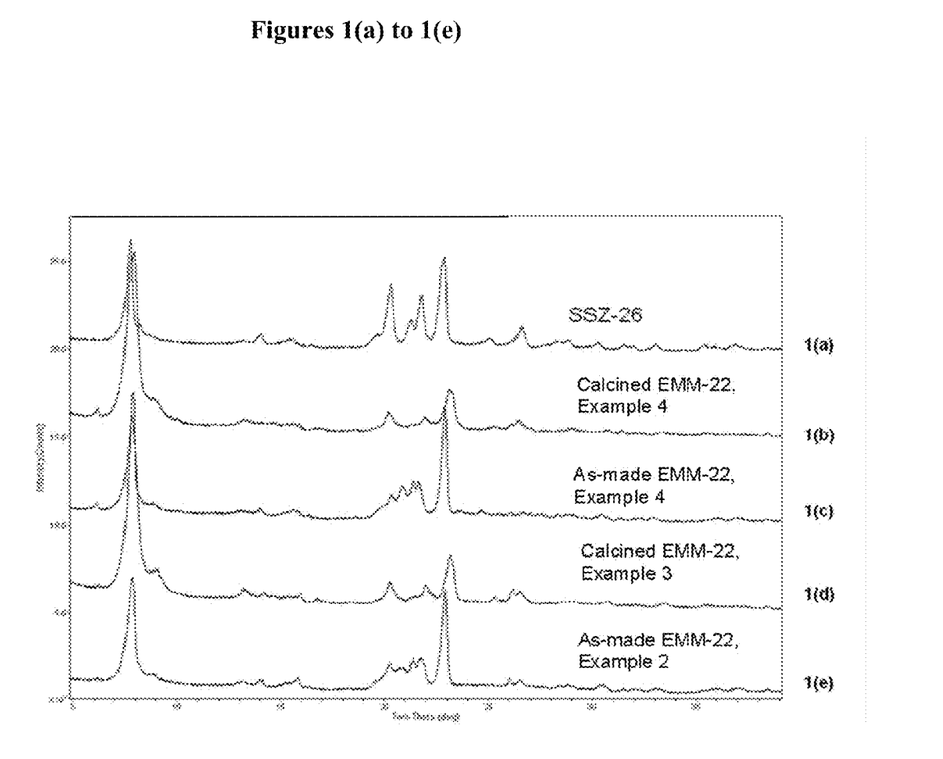
FIG. 1(a) shows the X-ray diffraction pattern of SSZ-26.
FIG. 1(e) shows the X-ray diffraction pattern of the as-synthesized molecular sieve material of Example 2 of the present disclosure.
Figure 2A:
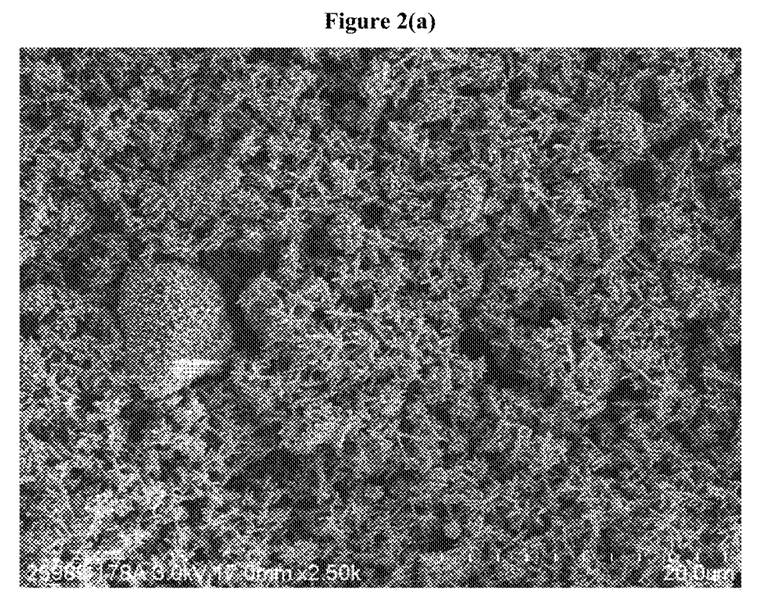
FIGS. 2(a) to 2(d) are scanning electron micrograph (SEM) images of the product of Example 2 of the present disclosure at different magnifications.
Figure 2B:
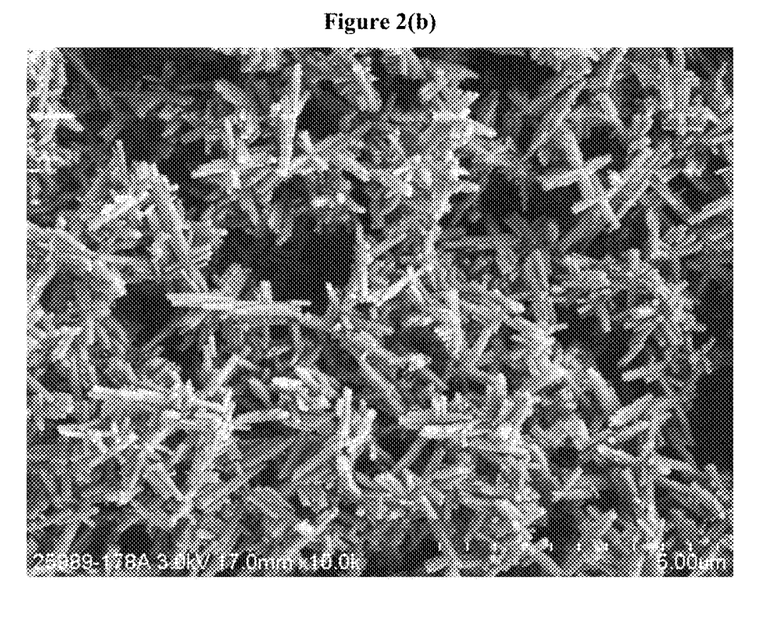
Figure 2C:
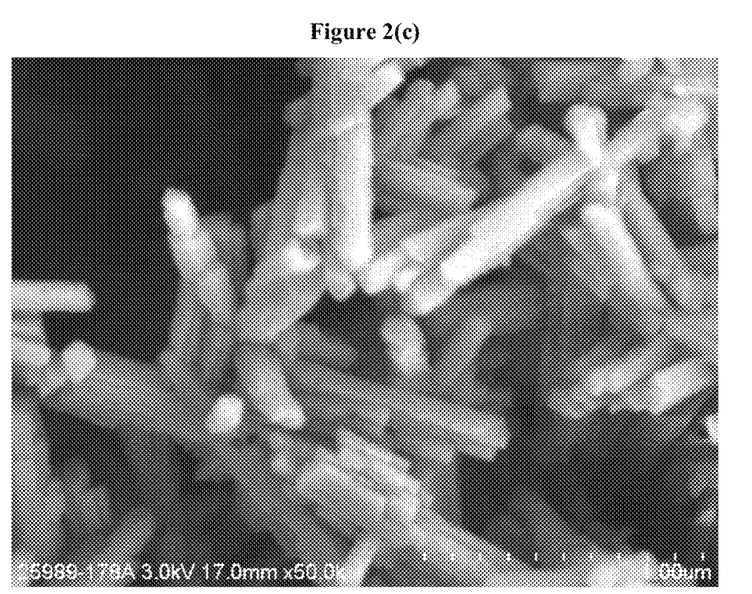
Figure 2D:
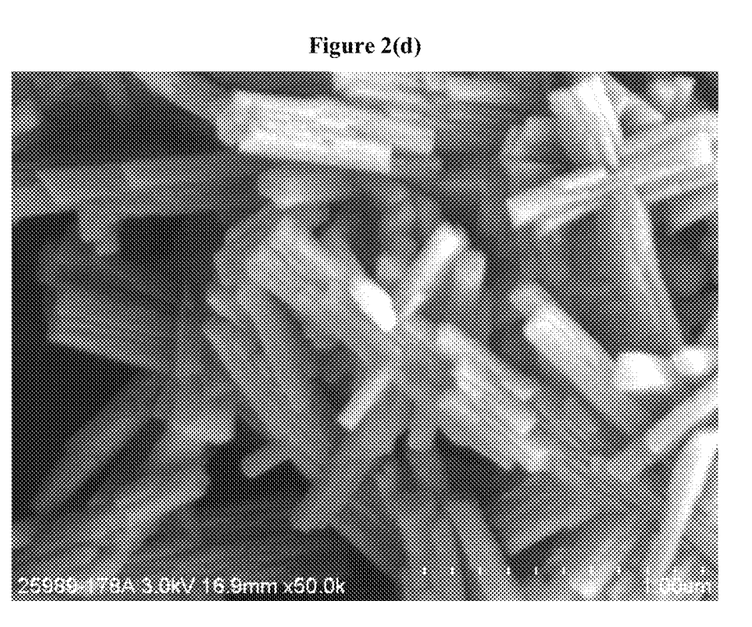

The X-ray diffraction pattern for SSZ-26 can be found in FIG. 1(a) of the present disclosure.

U.S. Pat. No. 7,648,694 describes a process for preparing zeolites of the SSZ-26/33 family using a structure directing agent (SDA) selected from the group consisting of 1,5-bis(N, N-dimethylcyclohexylammonium)pentane dications, 1,4-bis(N-cyclohexylpiperidinium)butane dications and 1,4-bis(N-cyclopentylpiperidinium)butane dications. The entire disclosure of U.S. Pat. No. 7,648,694 is incorporated herein by reference.

According to the present invention, it has now been found that a novel zeolite having an X-ray diffraction pattern which is similar to, but nonetheless distinct from, both the experimental and the simulated patterns of the SSZ-26/33 family of zeolites can be prepared using 1,4-bis(N-isopentylpyrrolidinium)butane dications as the structure directing agent and zeolite Y as an aluminum source. The new zeolite possesses a large micropore volume of 0.24 cc/g, which is higher than the typically measured 0.19-0.21 cc/g for SSZ-26/33 type zeolites.

SUMMARY

In one aspect, the present disclosure provides a molecular sieve material, designated EMM-22, having, in its as-calcined form, an X-ray diffraction pattern including the following peaks in Table 1:

TABLE 1

| d-spacing (Å) | Relative Intensity [100 × I/I(o)] |
|---|---|
| 11.03 ± 0.40 | VS |
| 9.91 ± 0.20 | W |
| 6.70 ± 0.04 | VW |
| 4.39 ± 0.02 | W |
| 4.06 ± 0.04 | W |
| 3.85 ± 0.02 | M |
| 3.37 ± 0.02 | S |

Conveniently, the calcined molecular sieve material has a composition comprising the molar relationship:

$$X_2O_3:(n)YO_2,$$

wherein n is at least about 20, X is a trivalent element, such as one or more of B, Al, Fe, and Ga, especially Al, and Y is a tetravalent element, such as one or more of Si, Ge, Sn, Ti, and Zr, especially Si.

The present disclosure also provides a molecular sieve material having, in its as-synthesized form, an X-ray diffraction pattern including the following peaks in Table 2:

TABLE 2

| d-spacing (Å) | Relative Intensity [I/I(o)] |
|---|---|
| 11.23 | S |
| 10.04 | W |
| 6.79 | VW |
| 6.32 | W |
| 5.82 | W |
| 5.68 | W |
| 4.46 | W |
| 4.37 | M |
| 4.26 | M |
| 4.16 | M |
| 4.10 | M |
| 3.88 | S |

In embodiments, the as-synthesized molecular sieve material has a composition comprising the following molar relationship:

$$mQ:X_2O_3:(n)YO_2,$$

wherein 0<m≤0.2; n is at least about 20; Q is an organic structure directing agent; X is a trivalent element, such as one or more of B, Al, Fe, and Ga, especially Al; and Y is a tetravalent element, such as one or more of Si, Ge, Sn, Ti, and Zr, especially Si.

Conveniently, Q comprises 1,4-bis(N-isopentylpyrrolidinium)butane dications, which have the following formula:

In a further aspect, the present disclosure provides a process for producing the molecular sieve material described herein, the process comprising:

(i) preparing a synthesis mixture capable of forming said molecular sieve material, said mixture comprising a source of an alkali or alkaline earth metal (M), a source of an oxide of aluminum comprising zeolite Y, a separate source of silica, water, and a structure directing agent (Q) comprising 1,4-bis (N-isopentylpyrrolidinium)butane dications, and said mixture having a composition, in terms of mole ratios, within the following ranges:

| | |
|---|---|
| $SiO_2/Al_2O_3$ | at least 20; |
| $H_2O/SiO_2$ | about 15 to about 60; |
| $OH^-/SiO_2$ | about 0.20 to about 0.60; |
| $M/SiO_2$ | about 0.05 to about 0.50; and |
| $Q/SiO_2$ | about 0.05 to about 0.20; |

(ii) heating said mixture under crystallization conditions including a temperature of from about 120° C. to about 200° C. and a time from about 1 to about 28 days until crystals of said molecular sieve material are formed; and (iii) recovering said crystalline material from step (ii).

The present disclosure also provides a process for converting a feedstock comprising an organic compound to a conversion product which comprises the step of contacting said feedstock with a catalyst at organic compound conversion conditions, said catalyst comprising an active form of the molecular sieve material described herein.

BRIEF DESCRIPTION OF THE DRAWINGS

FIG. 1(b) shows the X-ray diffraction pattern of the calcined molecular sieve material of Example 4 of the present disclosure.

FIG. 1(c) shows the X-ray diffraction pattern of the as-synthesized molecular sieve material of Example 4 of the present disclosure.

FIG. 1(d) shows the X-ray diffraction pattern of the calcined molecular sieve material of Example 3 of the present disclosure.

DETAILED DESCRIPTION OF EMBODIMENTS

Described herein is a novel molecular sieve material, which is designated EMM-22, its synthesis in the presence of 1,4-bis(N-isopentylpyrrolidinium)butane dications as a structure directing agent and its use as an adsorbent and as a catalyst for organic conversion reactions.

In particular, the novel molecular sieve structure EMM-22 is characterized by an X-ray diffraction pattern which, in the as-calcined form of the molecular sieve, includes at least the peaks set out in Table 1 below and which, in the as-synthesized form of the molecular sieve, includes at least the peaks set out in Table 2 below.

TABLE 1

| d-spacing (Å) | Relative Intensity [100 × I/I(o)] |
|---|---|
| 11.03 ± 0.40 | VS |
| 9.91 ± 0.20 | W |
| 6.70 ± 0.04 | VW |

TABLE 1-continued

| d-spacing (Å) | Relative Intensity [100 × I/I(o)] |
|---|---|
| 4.39 ± 0.02 | W |
| 4.06 ± 0.04 | W |
| 3.85 ± 0.02 | M |
| 3.37 ± 0.02 | S |

TABLE 2

| d-spacing (Å) | Relative Intensity [I/I(o)] |
|---|---|
| 11.23 | S |
| 10.04 | W |
| 6.79 | VW |
| 6.32 | W |
| 5.82 | W |
| 5.68 | W |
| 4.46 | W |
| 4.37 | M |
| 4.26 | M |
| 4.16 | M |
| 4.10 | M |
| 3.88 | S |

The X-ray diffraction data reported herein were collected with a PANalytical X-Pert Pro diffraction system, equipped with an X'Celerator detector, using copper K-alpha radiation. The diffraction data were recorded by step-scanning at 0.017 degrees of two-theta, where theta is the Bragg angle, and a counting time of 21 seconds for each step. The interplanar spacings, d-spacings, were calculated in Angstrom units, and the relative peak area intensities of the lines, I/Io, is one-hundredth of the intensity of the strongest line, above background, were determined with the MDI Jade peak profile fitting algorithm. The intensities are uncorrected for Lorentz and polarization effects. The relative intensities are given in terms of the symbols VS=very strong (greater than 60 to 100), S=strong (greater than 40 to 60), M=medium (greater than 20 to 40), W=weak (4 to 20) and VW=very weak (0 to 4).

It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

In its calcined form, molecular sieve EMM-22 has a chemical composition comprising the molar relationship:

$$X_2O_3:(n)YO_2,$$

wherein n is at least 20, such as at least 25, at least 30 or at least 40, X is a trivalent element, such as one or more of B, Al, Fe, and Ga, especially Al, and Y is a tetravalent element, such as one or more of Si, Ge, Sn, Ti, and Zr, especially Si. It will be appreciated from the permitted values for n that EMM-22 can be synthesized in totally siliceous form in which the trivalent element X is absent or essentially absent.

In its as-synthesized and anhydrous form, molecular sieve EMM-22 has a chemical composition comprising the molar relationship:

$$mQ:X_2O_3:(n)YO_2,$$

wherein $0<m\leq0.2$, n is at least about 10, typically greater than about 20, Q is an organic structure directing agent, X is a trivalent element, such as one or more of B, Al, Fe, and Ga, especially Al and Y is a tetravalent element, such as one or more of Si, Ge, Sn, Ti, and Zr, especially Si.

Conveniently, Q comprises 1,4-bis(N-isopentylpyrrolidinium)butane dications, which have the following formula:

The Q component, which is associated with the as-synthesized material as a result of their presence during crystallization, are easily removed by conventional post-crystallization methods or by treatment with ozone (see, e.g., Parikh et al., Microporous and Mesoporous Materials 76 (2004) 17-22).

The molecular sieve EMM-22 is thermally stable and in the calcined form exhibits a high surface area and significant hydrocarbon sorption capacity.

In illustrative embodiments, aluminosilicate EMM-22 can be prepared from a synthesis mixture comprising a source of an alkali or alkaline earth metal (M), a source of an aluminum oxide comprising zeolite Y, a separate source of silica, water, and a structure directing agent (Q) as described above, the synthesis mixture having a composition, in terms of mole ratios of oxides, within the following ranges:

| Reactants | Useful | Preferred |
|---|---|---|
| $SiO_2/Al_2O_3$ | at least 20 | at least 30 |
| $H_2O/SiO_2$ | 15-60 | 20-40 |
| $OH^-/SiO_2$ | 0.20-0.60 | 0.20-0.50 |
| $M/SiO_2$ | 0.05-0.50 | 0.10-0.50 |
| $Q/SiO_2$ | 0.03-0.20 | 0.05-0.20 |

Suitable sources of aluminum in addition to zeolite Y include hydrated alumina, aluminum hydroxide, alkali metal aluminates, aluminum alkoxides, and water-soluble aluminum salts, such as aluminum nitrate. Suitable sources silica include colloidal suspensions of silica, precipitated silica, fumed silica, alkali metal silicates, and tetraalkyl orthosilicates.

Suitable sources of Q are the hydroxides and/or salts of the relevant diquaternary ammonium compounds. 1,4-bis(N-isopentylpyrrolidinium)butane dications can readily be synthesized by reaction of N-isopentylpyrrolidine with 1,4-dibromobutane. N-isopentylpyrrolidine is conveniently prepared by the reductive amination of isovaleraldehyde with pyrrolidine.

Crystallization of EMM-22 can be carried out at either static or stirred conditions in a suitable reactor vessel, such as for example, polypropylene jars or teflon lined or stainless steel autoclaves, at a temperature of about 100° C. to about 200° C., such as 120° C. to 160° C., for a time sufficient for crystallization to occur at the temperature used, e.g., from about 1 day to about 28 days. Thereafter, the crystals are separated from the liquid and recovered.

To the extent desired and depending on the $Al_2O_3/SiO_2$ molar ratio of the material, any cations in the as-synthesized EMM-22 can be replaced in accordance with techniques well known in the art by ion exchange with other cations.

Illustrative examples of suitable replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups 2 to 15 of the Periodic Table of the Elements. As used herein, the numbering scheme for the Periodic Table Groups is as disclosed in Chemical and Engineering News, 63(5), 27 (1985).

The molecular sieve material in embodiments of the present disclosure may also be subjected to treatment to remove part of or all of the organic directing agent Q that was used in its synthesis. This may be accomplished by thermal treatment in which the as-synthesized material is heated at a temperature of at least about 370° C. for at least 1 minute and generally not longer than 20 hours or by treatment with ozone as described by Parikh et al. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g., hydrocarbon, conversion reactions.

The present molecular sieve may be intimately combined with a hydrogenating component, such as molybdenum, rhenium, nickel, cobalt, chromium, manganese, or a noble metal such as platinum or palladium where a hydrogenation-dehydrogenation function is to be performed. Such a component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The present molecular sieve, when employed either as an adsorbent or as a catalyst should be dehydrated, at least partially. The dehydration can be done by heating the molecular sieve to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the EMM-22 in a vacuum, but a longer time is required to obtain a sufficient amount of dehydration.

The present molecular sieve can also be used as an adsorbent or, particularly in its aluminosilicate form, as a catalyst to catalyze a wide variety of organic compound conversion processes including many of present commercial/industrial importance. Examples of chemical conversion processes which are effectively catalyzed by the crystalline material of the present disclosure, by itself or in combination with one or more other catalytically active substances including other crystalline catalysts, include those requiring a catalyst with acid activity. Illustrative examples of organic conversion processes which may be catalyzed by EMM-22 include but are not limited to: cracking, hydrocracking, disproportionation, alkylation, oligomerization, and isomerization.

As in the case of many catalysts, it may be desirable to incorporate EMM-22 with another material that is resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels, including mixtures of silica and metal oxides. Use of a material in conjunction with EMM-22, i.e., combined therewith or present during synthesis of the new crystal, which is active, tends to change the conversion and/or selectivity of the catalyst in certain organic conversion processes.

Moreover, inactive materials suitably serve as diluents to control the amount of conversion in a given process so that products can be obtained in an economic and orderly manner without employing other means for controlling the rate of reaction. Such inactive materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with EMM-22 include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

Binders useful for compositing with EMM-22 also include inorganic oxides, such as silica, zirconia, titania, magnesia, beryllia, alumina, and mixtures thereof.

In addition to the foregoing materials, EMM-22 can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of EMM-22 and the inorganic oxide matrix may vary widely, with the EMM-22 content ranging from about 1 to about 90 percent by weight and more usually, particularly when the composite is prepared in the form of beads, in the range of about 2 to about 80 weight percent of the composite.

The invention will now be more particularly described with reference to the following non-limiting Examples and the accompanying drawings.

As used in the Examples, alpha value is a measure of the acid activity of a zeolite catalyst as compared with a standard silica-alumina catalyst. The alpha test is described in U.S. Pat. No. 3,354,078; in the Journal of Catalysis, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the Journal of Catalysis, Vol. 61, p. 395. The higher alpha values correspond with a more active cracking catalyst.

The XRD patterns reported in the Examples were recorded as described above, whereas the SEM data were collected on a Hitachi S4800 microscope. Elemental analysis was determined by inductively coupled plasma atomic emission spectrometry.

Example 1

Preparation of 1,4-bis(N-isopentylpyrrolidinium)butane dications 500 mL tetrahydrofuran (THF) was placed in a 1-L suction flask. 35.3 g isovaleraldehyde (0.41 mol) and then 28.4 g pyrrolidine (0.40 mol) were mixed into the THF. 100 g of sodium triacetoxyborohydride (0.47 mol) powder was then added in 5-10 g increments to the solution. During the addition vigorous stirring was used to ensure that the powder did not clump at the bottom of the flask which would prevent the efficient mixing of the suspension. After each addition of the sodium triacetoxyborohydride powder, adequate time was provided to form a uniform slurry before the next addition of the powder. After one day the product was worked up by quenching the suspension with the slow addition of 291 g of a 27% KOH solution. The product was then extracted from the resultant solution with 500 mL pentane. The organic fraction was then collected with a separatory funnel and dried with anhydrous magnesium sulfate. The N-isopentylpyrrolidine product was then isolated by rotary evaporation of the THF and pentane solvents under reduced pressure.

15.0 g of the resultant N-isopentylpyrrolidine (0.13 mol) was added to 60 mL acetonitrile inside a 125-mL Teflon liner. 12.35 g 1,4-dibromobutane (0.057 mol) was added to the mixture. The liner was then capped, sealed inside a Parr steel autoclave, and then heated at 80° C. for 4 days. The solid precipitates were then collected by filtration and washed with acetone. After the acetone wash, additional product precipitated within the filtrate. The combined solids were then washed with ether and allowed to dry. The total yield of clean product was 19.5 g. $^1$H and $^{13}$C NMR showed the product to be pure. The dibromide salt was then ion-exchanged into the hydroxide form by dissolving it in water and passing it through a column of Dowex LC NG hydroxide exchange resin. The concentration of the aqueous solution was determined by titration with a standard solution of 0.1 N HCl.

Example 2

Synthesis of EMM-22

A synthesis gel with molar ratios of $H_2O/SiO_2=38.3$ and Si/Al=18 was prepared according to the following procedure.

2.41 g of a hydroxide solution of 1,4-bis(N-isopentylpyrrolidinium)butane ([OH]=0.85 mmol/g) produced as in Example 1 was mixed with 2.33 g 1N NaOH and 2.33 g deionized water within a 23-mL Teflon liner. 0.48 g Cabosil M-5 fumed silica (obtained from Cabot Corporation) and 0.15 g of sodium form of zeolite Y (Si/Al=2.5 and obtained from Contract Materials Processing, Inc) were then mixed into the solution to create a uniform suspension. The liner was then capped and sealed within a 23 mL steel Parr autoclave. The autoclave was placed on a spit within a convection oven at 160° C. The autoclave was tumbled at 50 rpm over the course of 17 days inside the heated oven. The autoclave was then removed and allowed to cool to room temperature. The solids were then recovered by filtration and washed thoroughly with deionized water (>250 mL) and then acetone (about 20 mL).

The solids were allowed to dry in an oven at 100° C. for 2 hours. The resulting product was analyzed by powder XRD and shown to be EMM-22 with a trace level of zeolite Y reactant and a trace level of analcime. The XRD pattern is shown in FIG. 1(e). FIGS. 2(a) to 2(d) show SEM images of the product.

Example 3

Calcination of EMM-22

A portion of the product from Example 2 was calcined according to the following procedure.

The zeolite was heated inside a muffle furnace from ambient temperature to 400° C. at 4° C./min under a nitrogen atmosphere, then heated to 600° C. at 4° C./min in air, and maintained at 600° C. in air for 2 hours. The XRD pattern of the calcined material is shown in FIG. 1(d). 0.23 g of the calcined material was then added to a solution created by dissolving 2.3 g ammonium nitrate in 23 g deionized water. The solution was heated overnight in a steambox at 98° C. The zeolite was then recovered by filtration and washed three times with 60-mL deionized water.

The sample was then allowed to dry in an oven. The sample was then calcined to 500° C. to obtain the fully acidic form of the zeolite. From nitrogen physisorption experiments, it was determined that this sample possesses a micropore volume of 0.24-0.25 cc/g. This micropore volume is similar to those reported for zeolite beta, and is higher than those cited for SSZ-26/33 type zeolites (0.19-0.21 cc/g).

Example 4

Synthesis of EMM-22

A synthesis gel with molar ratios of Si/Al=15.5 and $H_2O/SiO_2=38.3$ was prepared according to the following procedure.

25.54 g of a hydroxide solution of 1,4-bis(N-isopentylpyrrolidinium)butane ([OH]=0.96 mmol/g) produced as in Example 1 was mixed with 21.49 g 1 N NaOH, 27.82 g deionized water, 5.73 g Cabosil M-5 fumed silica, and 1.79 g of the sodium form of zeolite Y (Si/Al=2.5). The reactant gel was placed within a Teflon liner for a 125-mL steel Parr autoclave, and the liner was then capped and sealed inside the steel Parr autoclave. The autoclave was placed on a spit within a convection oven at 160° C.

The autoclave was tumbled at 50 rpm over the course of 5 days inside the heated oven. The autoclave was then removed and allowed to cool to room temperature. The solids were then recovered by filtration and washed thoroughly with deionized water (>500 mL) and then acetone (about 40 mL). The solids were allowed to dry overnight in a vacuum oven at 65° C.

The yield of as-made product was 6.62 g. The resulting product was analyzed by powder XRD and shown to be EMM-22 with a trace level of zeolite Y reactant and a trace level of analcime. The XRD pattern of the as-made product of Example 4 can be found in FIG. 1(c) and the powder diffraction peak intensities and positions can be found in Table 3.

TABLE 3

| 2-Theta (degrees) | d-spacing (Å) | I/Io |
|---|---|---|
| 7.87 | 11.23 | 1.00 s |
| 8.80 | 10.04 | 0.07 w |

TABLE 3-continued

| 2-Theta (degrees) | d-spacing (Å) | I/Io |   |
|---|---|---|---|
| 13.03 | 6.79 | 0.03 | vw |
| 14.00 | 6.32 | 0.07 | w |
| 15.22 | 5.82 | 0.04 | w |
| 15.59 | 5.68 | 0.06 | w |
| 19.89 | 4.46 | 0.11 | w |
| 20.29 | 4.37 | 0.20 | m |
| 20.85 | 4.26 | 0.27 | m |
| 21.33 | 4.16 | 0.32 | m |
| 21.63 | 4.10 | 0.31 | m |
| 22.88 | 3.88 | 0.93 | s |

The resulting product was then calcined, ammonium-exchanged, and recalcined using a procedure corresponding to the procedure described above in Example 3. The XRD pattern of the as-calcined material of Example 4 can be found in FIG. 1(b).

Example 5

Testing of EMM-22

The calcined product of Example 4 was tested for its capacity to adsorb n-hexane at 90° C. and 2,2-dimethylbutane and 2,3-dimethylbutane at 120° C. The results are summarized below:

| n-hexane | 99 mg/g |
|---|---|
| 2,2-dimethytlbutane | 81 mg/g |
| 2,3-dimethylbutane | 87 mg/g |

The Si/Al determined from ICP analysis is 15.5.
The sample shows an alpha of 750.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A molecular sieve material having, in its as-calcined form, an X-ray diffraction pattern including the following peaks in Table 1:

TABLE 1

| d-spacing (Å) | Relative Intensity [100 × I/I(o)] |
|---|---|
| 11.03 ± 0.40 | VS |
| 9.91 ± 0.20 | W |
| 6.70 ± 0.04 | VW |
| 4.39 ± 0.02 | W |
| 4.06 ± 0.04 | W |
| 3.85 ± 0.02 | M |
| 3.37 ± 0.02 | S. |

2. The molecular sieve material of claim 1, and having a composition comprising the molar relationship $$X_2O_3:(n)YO_2,$$

wherein n is at least about 20, X is a trivalent element, and Y is a tetravalent element.

3. The molecular sieve material of claim 1, wherein X includes aluminum and Y includes silicon.

4. The molecular sieve material of claim 1, further comprising 1,4-bis(N-isopentylpyrrolidinium)butane dications in its pores.

5. The molecular sieve material of claim 1, having, after calcination to remove any organic material, a micropore volume of about 0.24 cc/g, as measured by nitrogen physisorption.

6. A catalyst comprising the molecular sieve of claim 1 and a binder.

7. A catalyst comprising the molecular sieve of claim 1 and a matrix material.

8. A process for converting a feedstock comprising an organic compound to a conversion product, the process comprising contacting said feedstock with a catalyst at organic compound conversion conditions, said catalyst comprising an active form of the molecular sieve material of claim 1.

9. A molecular sieve material having, in its as-synthesized form, an X-ray diffraction pattern including the following peaks in Table 2:

TABLE 2

| d-spacing (Å) | Relative Intensity [I/I(o)] |
|---|---|
| 11.23 | S |
| 10.04 | W |
| 6.79 | VW |
| 6.32 | W |
| 5.82 | W |
| 5.68 | W |
| 4.46 | W |
| 4.37 | M |
| 4.26 | M |
| 4.16 | M |
| 4.10 | M |
| 3.88 | S. |

10. The molecular sieve material of claim 9, and having a composition comprising the following molar relationship:

$$mQ:X_2O_3:(n)YO_2,$$

wherein $0<m\leq0.2$; n is at least about 20; Q is an organic structure directing agent; X is a trivalent element and Y is a tetravalent element.

11. The molecular sieve material of claim 10, wherein X includes aluminum and Y includes silicon.

12. The molecular sieve material of claim 10, wherein Q comprises 1,4-bis(N-isopentylpyrrolidinium)butane dications.

13. A process for producing the molecular sieve material of claim 11, the process comprising the steps of:

(i) preparing a synthesis mixture capable of forming said molecular sieve material, said mixture comprising a source of an alkali or alkaline earth metal (M), a source of an oxide of aluminum comprising zeolite Y, a separate source of silica, water, and a directing agent (Q) comprising 1,4-bis(N-isopentylpyrrolidinium)butane dications, and said mixture having a composition, in terms of mole ratios, within the following ranges:

| $SiO_2/Al_2O_3$ | at least 20; |
|---|---|
| $H_2O/SiO_2$ | about 15 to about 60; |
| $OH^-/SiO_2$ | about 0.20 to about 0.60; |
| $M/SiO_2$ | about 0.05 to about 0.50; and |
| $Q/SiO_2$ | about 0.03 to about 0.20; |

(ii) heating said synthesis mixture under crystallization conditions including a temperature of from about 120°

C. to about 200° C. and a time from about 1 to about 28 days until crystals of said molecular sieve material are formed; and (iii) recovering said crystalline molecular sieve material from step (ii).

14. A molecular sieve material produced by the process of claim 10.

* * * * *